(12) United States Patent
Bosarge

(10) Patent No.: US 8,506,525 B2
(45) Date of Patent: Aug. 13, 2013

(54) WOUND SEALING FLUID DELIVERY APPARATUS AND METHOD

(75) Inventor: Patrick L. Bosarge, Mobile, AL (US)

(73) Assignee: University of South Alabama, Mobile, AL (US)

(*) Notice: Subject to any disclaimer, the term of this patent is extended or adjusted under 35 U.S.C. 154(b) by 218 days.

(21) Appl. No.: 12/927,369

(22) Filed: Nov. 12, 2010

(65) Prior Publication Data

US 2012/0053620 A1    Mar. 1, 2012

Related U.S. Application Data

(60) Provisional application No. 61/281,026, filed on Nov. 12, 2009.

(51) Int. Cl.
*A61M 1/06* (2006.01)

(52) U.S. Cl.
USPC ............................................. 604/73

(58) Field of Classification Search
USPC .............. 604/47, 73, 103.03, 167.06, 321, 604/543; 606/213, 214, 215
See application file for complete search history.

(56) References Cited

U.S. PATENT DOCUMENTS

| | | | |
|---|---|---|---|
| 4,381,765 A * | 5/1983 | Burton | 600/32 |
| 4,553,967 A * | 11/1985 | Ferguson et al. | 604/317 |
| 5,192,301 A * | 3/1993 | Kamiya et al. | 606/213 |
| 5,372,589 A * | 12/1994 | Davis | 604/180 |
| 5,833,665 A * | 11/1998 | Bootman et al. | 604/180 |
| 6,117,386 A * | 9/2000 | Stiger | 264/526 |
| 6,371,974 B1 * | 4/2002 | Brenneman et al. | 606/213 |
| 2003/0060802 A1 * | 3/2003 | Omaleki et al. | 604/528 |
| 2005/0107826 A1 * | 5/2005 | Zhu et al. | 606/213 |
| 2008/0234726 A1 * | 9/2008 | Biddle et al. | 606/213 |

\* cited by examiner

*Primary Examiner* — Aarti Bhatia Berdichevsky
(74) *Attorney, Agent, or Firm* — J. Nevin Shaffer, Jr.

(57) ABSTRACT

A wound sealing fluid delivery apparatus and method includes a surface seal. A catheter with a first end and a second end is provided such that the catheter passes through the surface seal. An infusion port is connected with the first end of the catheter and an expandable internal seal is connected with the catheter at the second end.

20 Claims, 2 Drawing Sheets

WOUND SEALING FLUID DELIVERY APPARATUS AND METHOD

CROSS REFERENCE TO RELATED APPLICATION

This application claims the benefit of previously filed U.S. provisional patent application No. 61/281,026 filed Nov. 12, 2009 for a "Wound Sealing Fluid Delivery Apparatus and Method". The Applicant hereby claims the benefit of this provisional application under 35 U.S.C. §119. The entire content of this provisional application is incorporated herein by this reference.

FIELD OF THE INVENTION

This invention relates to a wound sealing, fluid delivery apparatus and method. In particular, in accordance with one embodiment, the invention relates to a wound sealing fluid delivery apparatus including a surface seal. A catheter with a first end and a second end is provided such that the catheter passes through the surface seal. An infusion port is connected with the first end of the catheter and an expandable internal seal is connected with the catheter at the second end.

BACKGROUND OF THE INVENTION

A difficulty arises when a wound is diagnosed. With regard to penetrating trauma, by way of example only and not by way of limitation, wounds are created by objects which impale the body. These wounds include an observable external wound and additional unknown internal damage as well. Such injuries are caused by knives and guns, for example only.

Where the injury or wound is located determines what types of diagnostic assessments are currently available. If an injury, such as a stab wound to the anterior portion of the abdomen occurs, the current standard diagnostic assessment at many institutions is to lengthen the incision under local anesthesia to explore the internal wound to its base. If the wound penetrates deeper than the most anterior abdominal fascia, the outermost covering of the abdominal muscles, then some physicians perform an operation to determine if an injury has occurred within the abdominal cavity itself. Under this same scenario, however, some physicians perform an invasive procedure called a diagnostic peritoneal lavage ("DPL"). DPL is a procedure where a catheter is introduced into the abdomen and fluid is placed into the abdominal cavity. The fluid is then removed and sent for laboratory analysis. If the DPL is "positive" it means that the abdominal cavity has been penetrated and the patient is taken to the operating room for exploratory surgery; if "negative" the patient is admitted to the hospital for observation.

Penetrating trauma to the back and flanks is more problematic, however, because the posterior part of the abdomen, where structures such as the aorta, vena cava, kidneys, rectum, duodenum and pancreas are located, is not in communication with the abdominal cavity. This means that DPL assessments are useless in evaluating injuries in these locations. At a very minimum, therefore, patients with injuries in these locations will be admitted to the hospital for observation.

Thus, penetrating injuries produce a problematic scenario for physicians because without obvious signs that indicate the need for immediate exploration of the wound, a series of less than satisfactory diagnostic procedures are employed to try to delineate the extent of internal, underlying injuries in order to avoid unnecessary operations. The current state of medical practice includes imaging capabilities that have helped eliminate some "exploratory surgeries". For example, computerized tomography ("CT") is the leading diagnostic procedure of choice for trauma in general. However, traumatologists do not embrace CT evaluation for diagnosis of penetrating trauma due to the fear of missed injuries related to using a noncontrasted CT for evaluation of these injuries.

Thus, there is a need in the art for an apparatus and method to place radio-opaque contrast into traumatic wounds in order for CT delineation of both the depth and course of the tract of injury as well as potential injury to vital structures. Such an apparatus and method would enable physicians to diagnose patients suffering from penetrating trauma without the need for invasive procedures, such as wound exploration and DPL. Further, such a system would have other advantages including avoidance of non therapeutic operations and the possibility of discharge from hospital facilities directly out of the emergency department if the study is negative, thereby saving time, cost, resources and lives. It, therefore, is an object of this invention to provide an apparatus and method for placing radio opaque contrast fluid in a wound while sealing the wound and thus enabling CT evaluation of penetrating trauma quickly and inexpensively and without need for invasive diagnostic assessments.

SUMMARY OF THE INVENTION

Accordingly, the wound sealing fluid delivery apparatus of the present invention, according to one embodiment includes a surface seal. A catheter with a first end and a second end is provided and passes through the surface seal. An infusion port is connected with the first end of the catheter and an expandable internal seal is connected with the catheter at, meaning at least near, the second end.

As used herein, the term "wound" is given its common meaning to include wounds of all types and in animals and humans. The preferred embodiment of the invention is for use with penetrating wounds as discussed above but of course this is by way of example only and not by way of limitation. Likewise, the terms "catheter", "adhesive", "infusion port", "expandable", and "transparent" are given their common meaning as will become more apparent from the following discussion and descriptions.

In another aspect of the invention, the surface seal includes a transparent section and some adhesive. The adhesive may or may not be on the part of the seal that is transparent. In one aspect, the catheter is a flexible catheter. Again, as the term is used herein, "flexible" describes a catheter that is bendable and not overly stiff or rigid. A soft, rubber tube is acceptable, for example only.

In a further aspect, the surface seal includes an outer surface and a contact surface and the infusion port is connected with the catheter at or above the outer surface of the surface seal.

In one aspect, the surface seal includes an outer surface and a contact surface and an adhesive is located on a portion of the contact surface such that the adhesive surrounds a wound and creates a seal around the wound. In another aspect of the invention, an access port is connected with the expandable internal seal. In one aspect, the expandable seal includes transverse ridges. In further aspects, the catheter includes more than one opening at the second end and the surface seal is circular in shape with adhesive on a circumferential edge.

According to another embodiment of the invention, a wound sealing fluid delivery apparatus includes a surface seal with adhesive and a transparent section. A catheter with a first end and a second end passes through the surface seal. An infusion port is connected with the first end of the catheter, an expandable internal seal is connected with the catheter, and an access port is connected with the expandable internal seal.

According to another embodiment of the invention, a wound sealing fluid delivery method includes the steps of: providing a wound sealing fluid delivery device with a surface seal with adhesive, a catheter with a first end and a second end wherein the catheter passes through the surface seal, an infusion port connected with the first end of the catheter and an expandable internal seal connected with the catheter; inserting the catheter in a wound; sealing the wound with the surface seal with adhesive; expanding the expandable internal seal within the wound; and adding fluid at said infusion port such that fluid exits said catheter in said wound after said expandable internal seal.

Another aspect of the method includes an access port connected with the expandable internal seal for remotely expanding and contracting the expandable internal seal. In one aspect, the expandable seal includes transverse ridges and in a further aspect, the surface seal includes a transparent section as well as adhesive wherein the adhesive surrounds a wound and creates a seal around the wound.

DESCRIPTION OF THE DRAWINGS

Other objects, features and advantages of the present invention will become more fully apparent from the following detailed description of the preferred embodiment, the appended claims and the accompanying drawings in which:

DETAILED DESCRIPTION OF THE INVENTION

Figure 1:
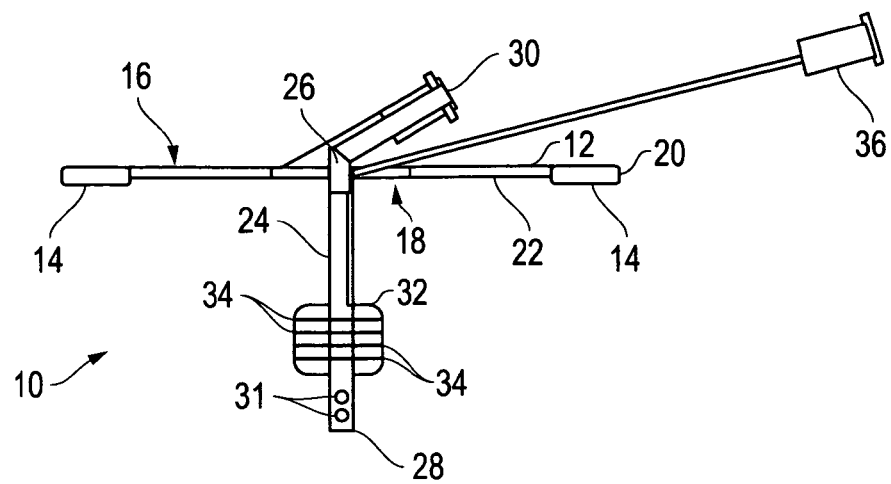
FIG. 1 is a side view of the wound sealing fluid delivery apparatus according to one embodiment.
Figure 2:
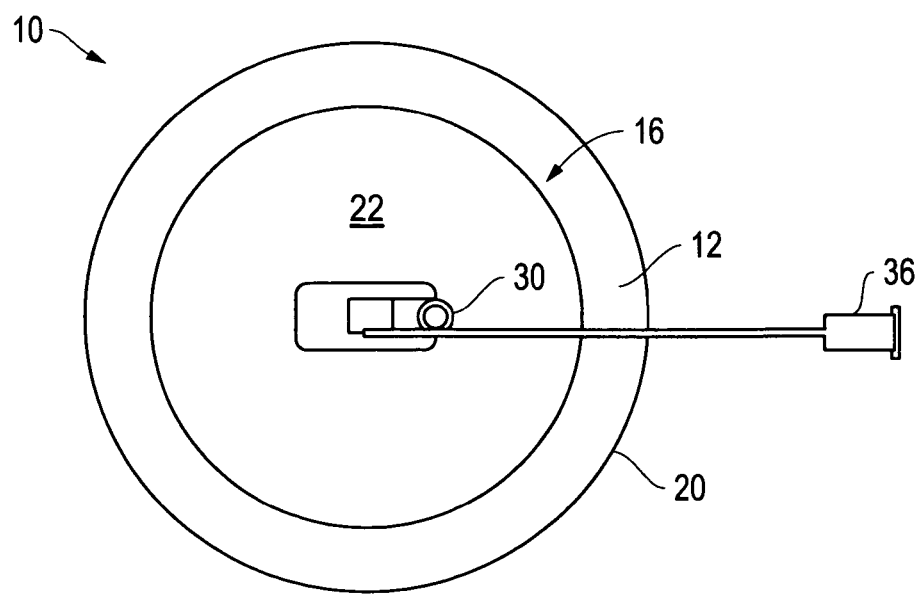
FIG. 2 is a top view of the invention of FIG. 1.

The preferred embodiment of the present invention is illustrated by way of example in FIGS. 1-2. With specific reference to FIG. 1, the wound sealing fluid delivery apparatus 10, according to a preferred embodiment, includes a surface seal 12 preferably with adhesive 14. It has been determined that with a sufficiently pliable surface seal, it may not be necessary to add adhesive to the surface seal in order for it to function adequately. Nonetheless, the Applicant has determined that at least some adhesive 14 is a preferred embodiment of the invention.

According to one aspect, surface seal 12 includes an upper or outer surface 16 and a lower or contact surface 18. Further, in one aspect, surface seal 12 is circular in shape (as more clearly shown in FIG. 2) and includes an outer circumference 20. In one aspect, adhesive 14 is provided on the contact surface 18 on the outer circumference 20. In another aspect, surface seal 12 includes a section 22 that is transparent so that the wound and skin surface, not shown, are visible through the transparent section. It may be useful to include adhesive 14 on transparent section 22 or not depending on the user's preference.

Preferably, surface seal 12 is made from a flexible, sterile material, such as plastic for example only and not by way of limitation. Adhesive 14 is any suitable adhesive known in the art that is compatible for human contact and that forms a seal between the skin surface and the contact surface 18 of the surface seal. It is this surface seal 12 that is the first of two seals provided by the present invention as will be discussed more fully hereafter.

A catheter 24, preferably made of soft, pliable, sterile, flexible, plastic, as is known in the art, passes though surface seal 12 as illustrated. Catheter 24 includes a first end 26 and a second end 28. First end 26 is connected with infusion port 30. Infusion port 30 receives fluid, not shown, such as radio opaque contrast fluid as is known in the art, and directs the fluid into the first end 26 of catheter 24. Thereafter, the fluid passes down catheter 24, and thereby through surface seal 12, and to the second end 28. Second end 28 includes at least one opening 31 as illustrated from which fluid passes as will be discussed more fully hereafter.

An expandable, internal seal 32 is connected with catheter 24 such that it surrounds catheter 24 nearer the second end 28 than the first end 26. Preferably, a portion of the second end 28 of catheter 24 extends beyond the expandable, internal seal 32 as illustrated in the Figure. By "expandable" it is understood that internal seal 32 is made of stretchable material that allows it, upon the application of pressure, to expand in size as does a rubber balloon, for example only. When expandable internal seal 32 is inserted in a wound and expanded, it forms a seal internally. This is the second of two seals provided by way of the present invention. That is, the first seal is formed on the outer surface of the body by surface seal 12. The second seal, within the wound and below the outer surface is formed by internal seal 32. Together, they cooperate to ensure that contrasting fluid introduced through infusion port 30, passes by the first and second seal and into the deepest part of the wound thereby, upon imaging, revealing the dimensions of the wound that have heretofore been invisible and extremely difficult to accurately ascertain.

In one aspect of the invention, expandable internal seal 32 includes transverse ridges 34 which greatly increase the sealing capacity of the internal seal 32. In another aspect, access port 36 is connected with expandable internal seal 32 such that pressure, air pressure for example only, may be introduced to or withdrawn from expandable internal seal 32 so as to easily enable expansion or reduction of the size of internal seal 32.

Figure 3:
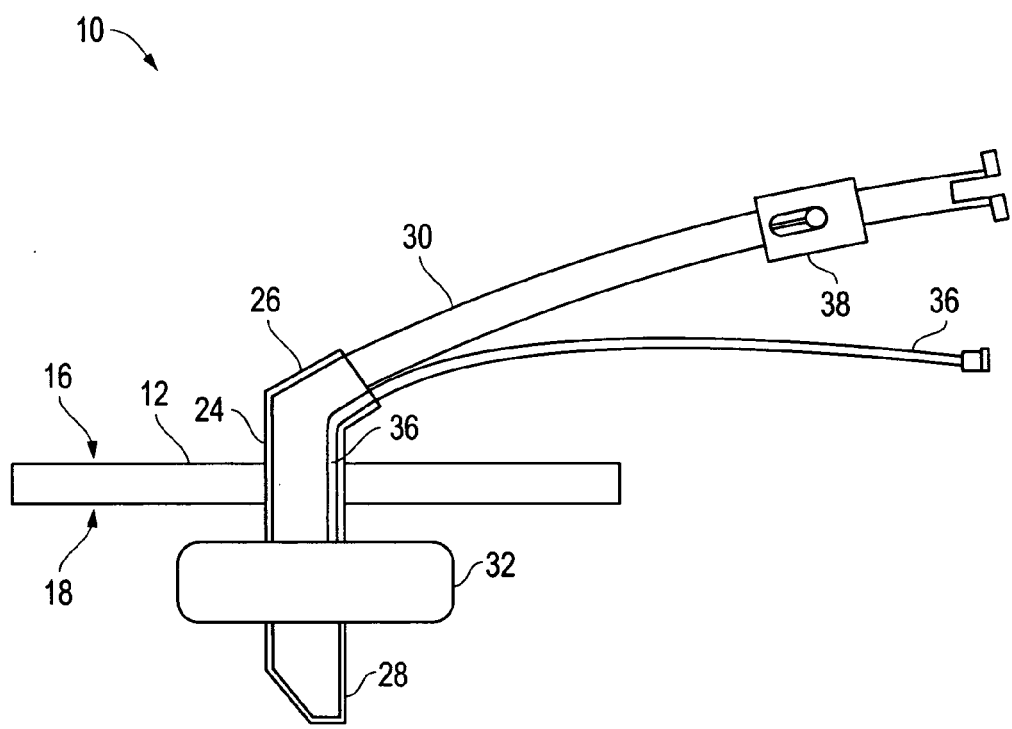
FIG. 3 is a side section view of another embodiment of the invention in which the access port is located within the catheter

FIG. 1 shows that the access port 36 is a tube connected with the internal seal 32. In this embodiment, access port 36 is located on the outside of catheter 24 and then with internal seal 32. FIG. 3, as will be discussed more fully hereafter, shows another embodiment in which the access port 36 is located within catheter 24 and connected through catheter 24 with the surrounding internal seal 32.

Referring now to FIG. 2, the reference numerals of FIG. 1 are repeated for the same elements in FIG. 2 in a top view. FIG. 2 clearly illustrates a preferred embodiment of the shape of the wound sealing fluid delivery apparatus 10 in circular form. Applicant has determined that this form is preferable because it enables a user to accurately and efficiently place the apparatus so as to seal the surface of the wound, the first seal of the invention. As the surface seal 12 is placed into position over the wound, catheter 24 and expandable internal seal 32 are placed within the wound. Thereafter, internal seal 32 is expanded within the wound, sealing it a second time but internally. This double seal is found to be extraordinarily and unexpectedly functional in enabling fluid, as discussed above, to be introduced into the wound and to the very limits of the wound. That is, the surface seal 12 in combination with the internal seal 32 allow fluid to be forced into the wound and not allowed to escape. In this way, fluid is forced into the entire wound and, by use of CT, all of the necessary details of the wound are made visible.

Referring now to FIG. 3, wound sealing fluid delivery apparatus 10 includes the same essential elements as discussed above. Here, however, the access port 36 is at least partially located within the catheter 24. Applicant has determined that this embodiment has the unexpected advantage of a catheter with an essentially smooth outer surface which appears to allow expandable internal seal to function more efficiently. Further, the location of the access port 36 tube within the catheter 24 reduces the number of transverse holes in surface seal 12 by half and appears to ensure a greater sealing effect by the first seal, surface seal 12.

Certainly, the location of access port 36 inside catheter 24 requires that the connection of access port 36 with expandable internal seal 32 pass through catheter 24. Nonetheless, this does not outweigh the above advantages.

FIG. 3, also illustrates another feature of the invention in the form of thumb lock 38. Thumb lock 38 is used by the practitioner to seal infusion port 30. The lock 38 closes infusion port 30 before and/or after use. When closed after use, it serves to ensure that fluid does not back flow out of the wound and out of infusion port 30. This is useful for keeping the fluid under pressure when inserted into the wound and to ensure, therefore, that an accurate image of the contour of the wound is observable.

Wound sealing fluid delivery apparatus and method 10 is simple in the make up of its basic parts including the surface seal 12, the soft, pliable plastic catheter 24 with the internal seal 32. Again, catheter 24 is designed to be placed into a wounding tract so that radio opaque contrast can be instilled into the wound. The expandable internal seal 32 at or near the tip of the catheter 24 inflates to seal the tract so that contrast can be instilled under pressure. This feature allows the course and depth of the wounding injury to be determined with the aid of an ordinary, non-invasive CT.

By way of continued explanation, Applicant's two seal apparatus ensures that the fluid can be delivered under pressure such that the entire wounding injury is identified. That is, the use of internal seal 32 alone is subject to failure due to the fact that a perfect internal seal is often difficult to obtain. The addition of transverse ridges 34 enhances internal sealing effectiveness. Nonetheless, the combination of surface seal 12 and internal seal 32 has been found to be most effective.

By way of further disclosure, Applicant has found that a contrast catheter with an outside wall thickness of 0.5 to 1 mm and an inside diameter of 2.5 to 3 mm is a preferred dimension for the effective operation of the invention. Likewise, an infusion port 36 has a preferred length of approximately 100 mm, the access port 36 a preferred length of approximately 100 to 150 mm and the surface seal 12 a diameter of approximately 80 mm. A surface seal 12 with a thickness of about 1 mm and a catheter 24 that extends below the contact surface 18 of surface seal 12 about 3 to 5 mm before the expandable internal seal 32 begins is most functional. Further, an expandable internal seal 32 that expands out from the catheter 24 a total of 80 mm from side to side and about 8 mm from the top to the bottom of expandable internal seal 32 functions best as a second, internal seal.

Further, Applicant has found that a catheter 24 second end 28 that extends 4 to 6 mm below the expandable internal seal 32 yields very satisfactory results. Additionally, it has been found acceptable for the first end 26 of catheter 24 to extend above the outer surface 16 of surface seal 12 by about 10 mm.

There are many practical advantages obtained by the present invention not the least of which is that it enables a user to inject radio opaque contrast fluid directly into the wound site fully and completely, under pressure and without leakage. This in turn allows the physician to accurately observe the depth and path of the penetrating injury. The enormous positive benefit this provides is that it eliminates unnecessary invasive procedures heretofore required for a competent assessment.

The description of the present embodiments of the invention has been presented for purposes of illustration, but is not intended to be exhaustive or to limit the invention to the form disclosed. Many modifications and variations will be apparent to those of ordinary skill in the art. As such, while the present invention has been disclosed in connection with an embodiment thereof, it should be understood that other embodiments may fall within the spirit and scope of the invention as defined by the following claims.

What is claimed is:

1. A wound sealing fluid delivery apparatus comprising:
   a) a surface seal having only a single passage and with an outer surface and a contact surface, said contact surface covering and sealing a skin surface such that fluid can not pass said surface seal;
   b) a catheter with a first end, a second end and one or more openings at said second end, wherein said catheter passes through said surface seal, and wherein said catheter forms the said single passage through said surface seal;
   c) an infusion port connected with said first end of said catheter; and
   d) an expandable internal seal connected with said catheter at said second end, said expandable internal seal conformed to expand to form a seal internally such that fluid can not pass said expandable internal seal, wherein fluid introduced to said first end of said catheter exits through said one or more openings at said second end of said catheter below said expandable internal seal to allow fluid to be forced into the wound and not be allowed to escape.

2. The apparatus of claim wherein said surface seal includes a transparent section and a portion of the surface seal includes adhesive.

3. The apparatus of claim 1 wherein said infusion port is connected with the catheter at or above the outer surface of the surface seal.

4. The apparatus of claim 1 wherein adhesive is located on a portion of said contact surface.

5. The apparatus of claim 1 further including an access port connected with said expandable internal seal.

6. The apparatus of claim 5 wherein said access port is a tube and wherein said tube is located within said catheter.

7. The apparatus of claim 1 wherein said expandable seal includes transverse ridges.

8. The apparatus of claim 1 wherein said catheter includes more than one opening at the second end.

9. The apparatus of claim 1 wherein said surface seal is circular in shape with adhesive on a circumferential edge.

10. A wound sealing fluid delivery apparatus comprising:
    a) a surface seal having only a single passage and with an outer surface and a contact surface, said contact surface covering and sealing a skin surface such that fluid can not pass said surface seal with adhesive on said contact surface and wherein said surface seal includes a transparent section;
    b) a catheter with a first end, a second end and one or more openings at said second end, wherein said catheter passes through said surface seal, and wherein said catheter forms the said single passage through said surface seal;
    c) an infusion port connected with said first end of said catheter; and d) an expandable internal seal connected with said catheter at said second end, said expandable internal seal conformed to expand to form a seal internally such that fluid can not pass said expandable internal seal, wherein fluid introduced to said first end of said catheter exits through said one or more openings at said second end of said catheter below said expandable internal seal to allow fluid to be forced into the wound and not be allowed to escape; and e) an access port connected with said expandable internal seal.

11. The apparatus of claim 10 wherein said wherein said catheter is a flexible catheter.

12. The apparatus of claim 10 wherein said infusion port is connected with the catheter at or above the outer surface of the surface seal.

13. The apparatus of claim 10 said adhesive is located on a portion of said contact surface such that said adhesive surrounds a wound and creates an adhesive seal around said wound.

14. The apparatus of claim 10 wherein said expandable seal includes transverse ridges.

15. The apparatus of claim 10 wherein said catheter includes more than one opening at the second end.

16. The apparatus of claim 10 wherein said surface seal is circular in shape with adhesive on a circumferential edge.

17. A wound sealing fluid delivery method comprising:

a) providing a wound sealing fluid delivery device with a surface seal having only a single passage and with an outer surface and a contact surface, said contact surface covering and sealing a wound on a said surface such that fluid can not pass said surface seal, a catheter with a first end, a second end and one or more openings at said second end, wherein the catheter passes through said surface seal, and wherein said catheter forms the said single passage through said surface seal; port connected with said first end of said catheter and an expandable internal seal connected with said second end of said catheter, said expandable internal seal conformed to expand to form a seal internally such that fluid can not pass said expandable internal seal, wherein fluid introduced to said first end of said catheter exits through said one or more openings at said second end of said catheter below said expandable internal seal to allow fluid to be forced into the wound and not be allowed to escape;

b) inserting said catheter in said wound;

c) sealing said wound with said surface seal;

d) expanding said expandable internal seal within said wound; and e) adding fluid at said infusion port such that fluid exits said catheter in said wound after said expandable internal seal.

18. The method of claim 17 further including an access port connected with said expandable internal seal for remotely expanding and contracting said expandable internal seal.

19. The method of claim 17 wherein said expandable seal includes transverse ridges.

20. The method of claim 17 wherein said surface seal includes a transparent section and adhesive wherein said adhesive surrounds a wound and creates a an adhesive seal around said wound.

* * * * *

UNITED STATES PATENT AND TRADEMARK OFFICE
CERTIFICATE OF CORRECTION

PATENT NO. : 8,506,525 B2
APPLICATION NO. : 12/927369
DATED : August 13, 2013
INVENTOR(S) : Patrick L. Bosarge Page 1 of 1

It is certified that error appears in the above-identified patent and that said Letters Patent is hereby corrected as shown below:

In the Claims

Claim 2, column 6, line 36: Please change "apparatus of claim" to --apparatus of claim 1--.

Claim 17, column 7, line 31: Please change "wound on a said surface" to --wound on a skin surface--.

Claim 17, column 8, line 5: Please change "port connected" to --an infusion port connected--.

Signed and Sealed this
Fourth Day of March, 2014

Michelle K. Lee
*Deputy Director of the United States Patent and Trademark Office*